(12) United States Patent
Konieczka et al.

(10) Patent No.: US 10,627,378 B2
(45) Date of Patent: Apr. 21, 2020

(54) VOLATILE ORGANIC COMPOUND MONITORING SYSTEM

(71) Applicant: GreenAire Solutions, LLC, Batavia, IL (US)

(72) Inventors: John Konieczka, Barrington, IL (US); Ken Kubitz, Elburn, IL (US); Timothy Austin, Scotts, MI (US)

(73) Assignee: GreenAire Solutions, LLC, Batavia, IL (US)

( * ) Notice: Subject to any disclaimer, the term of this patent is extended or adjusted under 35 U.S.C. 154(b) by 17 days.

(21) Appl. No.: 16/148,812

(22) Filed: Oct. 1, 2018

(65) Prior Publication Data

US 2019/0101515 A1 Apr. 4, 2019

Related U.S. Application Data

(60) Provisional application No. 62/565,878, filed on Sep. 29, 2017.

(51) Int. Cl.
*G01N 33/00* (2006.01)
*G01N 21/64* (2006.01)

(52) U.S. Cl.
CPC ..... *G01N 33/0006* (2013.01); *G01N 33/0047* (2013.01); *G01N 21/645* (2013.01)

(58) Field of Classification Search
USPC ............ 250/435; 73/23.2, 29.01, 31.05; 454/229, 370
See application file for complete search history.

(56) References Cited

U.S. PATENT DOCUMENTS 5,267,897 A * 12/1993 Drees ............... F24F 11/00
454/229

\* cited by examiner

*Primary Examiner* — Kiet T Nguyen
(74) *Attorney, Agent, or Firm* — Davis, Brown, Koehn, Shors & Roberts, P.C.; Sean D. Solberg (57) ABSTRACT

Disclosed herein are volatile organic compound monitoring or detection systems and methods, including systems having both a reference air intake component and at least one air sample intake line. In certain embodiments, the systems provide for continuously repeating cycles of testing and calibration/recalibration. Further implementations relate to systems having two or more intake lines that can be positioned to take air samples at distances ranging from 5 feet to 200 feet or more apart.

20 Claims, 3 Drawing Sheets

VOLATILE ORGANIC COMPOUND MONITORING SYSTEM

CROSS-REFERENCE TO RELATED APPLICATION(S)

This application claims the benefit under 35 U.S.C. § 119(e) to U.S. Provisional Application 62/565,878, filed Sep. 29, 2017 and entitled "Volatile Organic Compound Monitoring System," which is hereby incorporated herein by reference in its entirety.

FIELD OF THE INVENTION

The present invention relates to sensor devices and systems for detecting and monitoring concentrations of volatile organic compounds in target air samples in target spaces such as rooms, buildings or highly sensitive equipment. Certain devices and systems are used in various industrial, medical, or research lab applications.

BACKGROUND OF THE INVENTION

Known sensor devices for monitoring volatile organic compounds ("VOCs") at low parts per million ("ppm") and ultra low parts per billion ("ppb") concentrations have been limited to effective use for only short durations of time as a result of certain limitations of the known devices. More specifically, the known sensors cannot accurately measure the concentration of the VOCs over time, because they malfunction within a fairly short period of time and require a recalibration to accurately measure the VOC concentration. This recalibration process is tedious and requires a considerable period of time to conduct.

Known ultraviolet ("UV") illumination systems for sensing VOCs operate by exciting electrons in VOC molecules from a lower to a higher orbital state with UV radiation. As the electrons drop back to a lower orbital state, they release a photon. Each of the known detection systems has a photon-sensitive sensor that detects the discharged photons, thereby providing a measure of the number of VOCs in the sample. One disadvantage of these known systems is that the excited VOC molecules are "sticky." That is, the excited molecules are prone to adherence to various surfaces. As a result of this adherence property, the excited VOC molecules, over a short period of time, begin to adhere to and eventually start to cover the surface of the UV-illumination device, thereby blocking at least some portion of the UV radiation that is necessary for the sensor to operate correctly. This ongoing and continually increasing reduction of the UV radiation generated by the device causes a continual decrease or reduction in the number of excited VOC molecules, thereby resulting in skewed VOC concentration measurements that increasingly differ from the actual VOC concentration in the sample.

This known sensor limitation has restricted the measuring of low concentrations of VOCs to short and infrequent intervals. As a result of this issue, long term monitoring of VOCs has not been possible to date.

There is a need in the art for an improved VOC monitoring system that can monitor VOCs over a longer period of time in comparison to known systems.

BRIEF SUMMARY OF THE INVENTION

Discussed herein are various VOC detection and monitoring systems.

In Example 1, a volatile organic compound ("VOC") monitoring system comprises a housing, a reference air intake component associated with the housing, the air intake component comprising an intake air purification device, an air sample intake system associated with the housing, the air sample intake system comprising at least one sample intake line, at least one valve coupled to the at least one sample intake line and the reference air intake component, an air pump fluidically coupled to the reference air intake component and the at least one intake link via the at least one valve, a detection assembly fluidically coupled to the air pump, and an exhaust component associated with the housing, the exhaust component comprising an exhaust air purification device fluidically coupled to the detection assembly.

Example 2 relates to the VOC monitoring system according to Example 1, wherein the at least one sample intake line comprises a first sample intake line and a second sample intake line.

Example 3 relates to the VOC monitoring system according to Example 2, wherein first and second sample intake lines are operably coupled to a piece of equipment.

Example 4 relates to the VOC monitoring system according to Example 3, wherein the piece of equipment is an incubator.

Example 5 relates to the VOC monitoring system according to Example 2, wherein the first sample intake line comprises a first intake opening disposed at a first location in a space and the second sample intake line comprises a second intake opening disposed at a second location in the space, wherein the first and second locations are separated by at least 5 feet.

Example 6 relates to the VOC monitoring system according to Example 5, wherein the first and second locations are separated by at least 50 feet.

Example 7 relates to the VOC monitoring system according to Example 2, wherein the at least one valve comprises a first valve coupled to the first sample intake line, the reference air intake component, and the air pump, and a second valve coupled to the second sample intake line and the first valve.

Example 8 relates to the VOC monitoring system according to Example 1, wherein the at least one valve comprises a first position in which the reference air intake component is in fluidic communication with the air pump, and a second position in which the first sample intake line is in fluidic communication with the air pump.

Example 9 relates to the VOC monitoring system according to Example 1, wherein the at least one sample intake line comprises a plurality of sample intake lines comprising a plurality of intake openings disposed at a plurality of locations.

In Example 10, a VOC detection system comprises a reference air intake system comprising an intake air purification device, a valve system comprising at least first and second valves, wherein the first valve is coupled to the intake air purification device, an air sample intake system comprising at least first and second sample intake lines, wherein the first sample intake line is coupled to the first valve and the second sample intake line is coupled to the second valve, a detection assembly coupled to the intake air purification device and the sample intake system, an air pump coupled to the intake air purification device, the sample intake system, and the detection assembly, an exhaust component comprising an exhaust air purification device coupled to the detection assembly, and a controller electronically coupled to the detection assembly. The detection assembly comprises an illumination lamp, and a photon-sensitive sensor.

Example 11 relates to the VOC detection system according to Example 10, wherein the first valve comprises a first position in which the intake air purification device is in fluidic communication with the air pump and the detection assembly, and a second position in which the first sample intake line is in fluidic communication with the air pump and the detection assembly.

Example 12 relates to the VOC detection system according to Example 11, wherein the second valve comprises a first position in which the second sample intake line is not in fluidic communication with the air pump and the detection assembly, and a second position in which the second sample intake line is in fluidic communication with the air pump and the detection assembly.

Example 13 relates to the VOC detection system according to Example 12, further comprising a third valve and a third sample intake line coupled to the third valve, wherein the third valve comprises a first position in which the third sample intake line is not in fluidic communication with the air pump and the detection assembly, and a second position in which the third sample intake line is in fluidic communication with the air pump and the detection assembly.

Example 14 relates to the VOC detection system according to Example 10, wherein the a detection assembly is configured to detect low parts per million VOC concentrations and ultra low parts per billion VOC concentrations.

In Example 15, a method of monitoring VOCs comprises positioning a VOC monitoring system such that the VOC monitoring system can receive samples from a target volume, calibrating the system by causing a calibration sample to pass through the intake purification device and the detection assembly, measuring a first zero reference reading with the detection assembly, and transmitting the first zero reference reading to the controller, testing an air sample by causing the air sample to pass through the at least one sample intake line and the detection assembly, measuring a sample reading with the detection assembly, transmitting the sample reading to the controller, and calculating a VOC concentration with the controller based on the sample reading and the first zero reference reading, recalibrating the system by causing a recalibration sample to pass through the intake purification device and the detection assembly, measuring a second zero reference reading with the detection assembly, and transmitting the second zero reference reading to the controller, and repeating the testing and recalibrating steps. The VOC monitoring system comprises an intake air purification device, at least one sample intake line, a detection assembly coupled to the intake air purification device and the at least one sample intake line, and a controller coupled to the detection assembly.

Example 16 relates to the method according to Example 15, wherein the causing the calibration sample to pass through the intake purification device and the detection assembly further comprises actuating a valve to move into a first position in which the intake purification device is in fluidic communication with the detection assembly, and actuating a pump to urge the calibration sample through the intake purification device and the detection assembly.

Example 17 relates to the method according to Example 16, wherein the causing the air sample to pass through the at least one sample intake line and the detection assembly further comprises actuating the valve to move into a second position in which the at least one sample intake line is in fluidic communication with the detection assembly, and actuating the pump to urge the air sample through the at least one sample intake line and the detection assembly.

Example 18 relates to the method according to Example 15, further comprising transmitting an alert to a user when the VOC concentration exceeds a predetermined level.

Example 19 relates to the method according to Example 18, further comprising establishing the predetermined level at an interface, wherein the interface is operably coupled with the controller.

Example 20 relates to the method according to Example 15, wherein the target volume is a volume in a piece of equipment, wherein the testing the air sample comprises testing a first air sample from an entrance of a filter and testing a second air sample from an exit of the filter, wherein the method further comprises tracking a life of the filter.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments herein relate to VOC monitoring systems and methods that can continuously and semi-continuously monitor VOCs in target air samples accurately for long durations, including, for example, up to and exceeding 1 year. More specifically, the various implementations include an internal process to automatically and repeatedly recalibrate the sensor, thereby maintaining the accuracy of the measured VOCs over a long period of time. Various embodiments disclosed or contemplated herein also allow for the measured data to be transmitted to and viewed via a secure website, mobile device application, or other known user interface or device. In certain implementations, the system can provide warning alerts to the interface or device if VOCs exceed preset limits.

Figure 1:
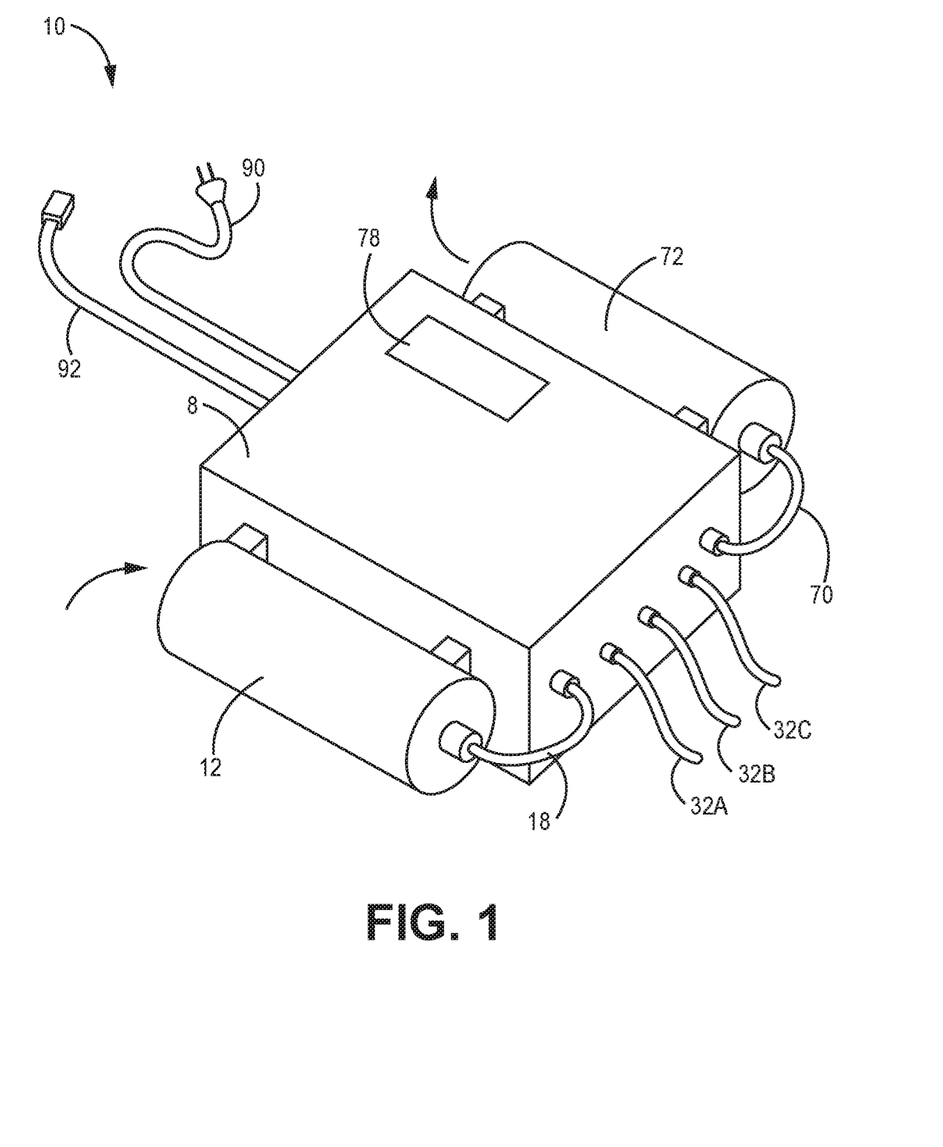
FIG. 1 is a perspective view of a VOC monitoring system according to one embodiment.
Figure 2:
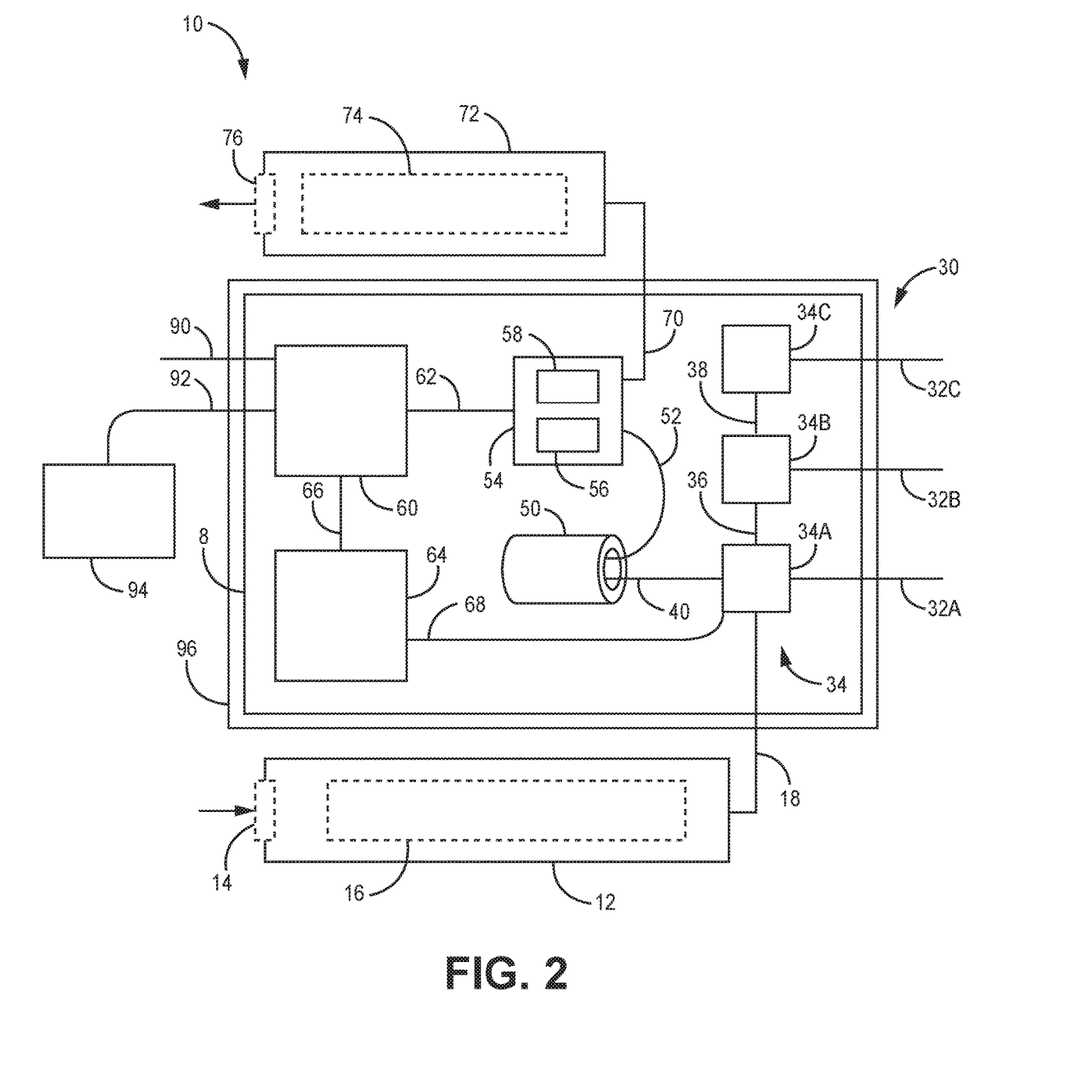
FIG. 2 is a schematic view of the VOC monitoring system of FIG. 1.

A VOC monitoring system 10 is depicted in FIGS. 1 and 2, according to one embodiment. FIG. 1 depicts the external features of the system 10, including a base unit (also referred to herein as a "housing") 8 with both an intake structure 12 and an exhaust structure 72 coupled thereto. A connection line 18 couples the intake structure 12 to the inner components of the housing 18, as will be described in further detail below. Similarly, a connection line 70 couples the exhaust structure 72 to the inner components of the base unit 18, as will also be described in further detail below. Further, the housing 8 in this exemplary implementation has a power cord 90 and a communication line 92 coupled thereto, along with three sample intake lines 32A, 32B, 32C. The base unit 8 also has an electronic or digital display 78.

As best shown in FIG. 2, which schematically depicts the components of the system 10, the intake structure 12 has an air intake port 14 and contains an intake filter 16. In one implementation, the intake filter 16 is a known "carbon zero" filter 16, which is a filter that is composed of carbon and other active compounds such that the filter eliminates all VOC's that may be contained within the air sample, ideally to a concentration of 0 ppb. The intake structure 12 is fluidically coupled to a first valve 34A (which will be discussed in further detail below) via a connection line 18. The intake filter 16, in one implementation, is used to purify air taken into the system 10 to create the purified reference air used for the calibration/recalibration process as described in further detail below.

In one embodiment, the connection line 18 is any tube, hose, or other similar component that provides a fluidically sealed connection between the intake structure 12 and the first valve 34A such that air can be transported therethrough from the structure 12 to the valve 34A. In further specific implementations, the connection line 18 is a component that has non-VOC off-gassing properties. In other words, the line 18 is made of a material that neither adds any impurities (including, for example, any VOCs) to the gas passing therethrough nor removes any such impurities therefrom. In one example, the connection line 18 is a Tygon® tubing product that has the desired non-VOC off-gassing properties. Alternatively, the line 18 can be made of copper, certain types of Teflon®, or any other known material that has the desired non-VOC off-gassing properties.

According to an alternative embodiment, the system 10 has no separate intake structure 12 and instead has an intake filter that is incorporated into the housing 8. In a further alternative, the various components of the system 10 can be incorporated into or associated with two or more base units, rather than a single base unit.

In addition, the system 10 in this embodiment has an air sample intake system 30 having intake lines (in this specific example, the three intake lines 32A, 32B, 32C mentioned above) and a valve system 34 (in this case, made up of three valves 34A, 34B, 34C). In the intake system 30, each of the intake lines 32A, 32B, 32C is fluidically coupled to the valve system 34, and more specifically to a separate valve 34A, 34B, 34C of the valve system 34. That is, as best shown in FIG. 2, the intake line 32A is coupled to valve 34A, intake line 32B is coupled to valve 34B, and intake line 32C is coupled to valve 34C. Each intake line 32A, 32B, 32C is any tube, hose, or other similar component that provides a fluidically sealed connection between the intake end of the tube (not shown) and the valve (34A, 34B, 34C, respectively) to which the line 32A, 32B, 32C is coupled such that air can be transported therethrough from the intake end of the tube (not shown) to the valve system 34. The intake lines 32A, 32B, 32C can be any line for transfer of gas or any other fluid, including the various types of lines described above with respect to the connection line 18, including any line having the non-VOC off-gassing properties discussed above. As such, each intake line 32A, 32B, 32C takes in air samples at the intake end (not shown) and transports the air to the system 10 through the line 32A, 32B, 32C as will be described in further detail below. In one embodiment, each line 32A, 32B, 32C is fluidically coupled to a pump 50 via the valve system 34 such that the pump 50 can create a vacuum to urge the air through each line 32A, 32B, 32C (or one or more lines 32A, 32B, 32C) toward the appropriate valve 34A, 34B, 34C depending on the settings of the various valves.

According to one embodiment as will be described in further detail below, the valve system 34 operates to control intake of either (1) reference (purified) air via the intake structure 12 for the calibration/recalibration process or (2) testing sample air via the intake system 30 for testing the air of the target area. That is, the various valves of the system 34 (in this case, valves 34A, 34B, 34C) are operated to control the flow of air from the appropriate intake source to perform repeating cycles of recalibration and testing as described elsewhere herein. Alternatively, the intake system 30 and valve system 34 can be configured in any known fashion for performing the repeating cycles as contemplated herein.

It is understood that while the current implementation has an intake system 30 with three intake lines 32A, 32B, 32C, the intake system 30 can have more than three. For example, in certain embodiments, the system 30 can have 4, 5, 6, 7, 8, 9, 10, or more intake lines. Regardless of the number of lines, according to various embodiments, each of the intake lines (such as lines 32A, 32B, 32C) can collect air from a different location. That is, the lines according to the various implementations disclosed or contemplated herein (such as lines 32A, 32B, 32C) have intake ends (not shown) that can be positioned in different predetermined locations at various distances from the system 10 in order to collect air samples from various distributed locations within an area, such as two or more different locations within a building, room, or the like. This sampling across multiple locations can generate a clearer picture of how the VOCs flow within an area (such as a room, for example) or how the VOCs are concentrated within that area. Further, in certain embodiments, this feature ensures that the system 10 doesn't simply sample air from one location immediately surrounding the system 10, which could result in an inaccurate measurement of the VOC concentration in the target room, building, or the other area in which the concentrations could vary across that specific area.

In accordance with certain implementations, each separate intake line (such as lines 32A, 32B, 32C) can have a different length in comparison to the other lines. Alternatively, two or more of the intake lines (such as lines 32A, 32B, 32C) can have the same length. The differing lengths of the lines in some embodiments make it possible for the intake end of each line 32A, 32B, 32C to be placed at a different, predetermined location at a different distance from the system 10, thereby ensuring collection of air samples from different locations in the area in which the air is being tested, as discussed above. In one implementation, any one or more of the lines (such as lines 32A, 32B, 32C) can have a length of at least about 100 feet. Alternatively, any one or more of the lines can have a length ranging from about 0.1 foot to about 10,000 feet or more. In a further alternative, any one or more of the lines has a length ranging from about 1 foot to about 1,000 feet. In yet another alternative, one or more of the lines has a length ranging from about 1 foot to about 500 feet. According to a further alternative embodiment, one or more of the lines has a length ranging from about 1 foot to about 200 feet. In accordance with an additional alternative, one or more of the lines has a length ranging from about 1 foot to about 175 feet. Alternatively, one or more of the lines can have any length within any of the ranges disclosed or contemplated herein. Further, each or any one of the lines can have any known length up to the dimensions of any target area (such as a room, building, or any other such area) such that samples can be collected from any location and various locations of varied distances within that target area.

In one embodiment, each of the valves 34A, 34B, 34C of the valve system 34 is separately coupled to a different one of the intake lines (32A, 32B, 32C, respectively) such that valve 34A is in fluidic communication with intake line 32A, valve 34B is in fluidic communication with intake line 32B, and valve 34C is in fluidic communication with intake line 32C. It is understood that each intake line (such as lines 32A, 32B, 32C) is coupled to a valve of the valve system 34 (such as valves 34A, 34B, 34C) in this fashion such that there are as many valves as there are intake lines. Thus, if there are four intake lines according to one exemplary embodiment, then there are four valves in the valve system 34. And this applies to any number of intake lines as described above.

According to certain embodiments and as best shown in FIG. 2, the valves 34A, 34B, 34C of the valve system 34 are also fluidically coupled to each other and to the pump 50. That is, in the specific exemplary implementation depicted in which the valve system 34 has three valves 34A, 34B, 34C, the valve 34C is fluidically coupled to valve 34B via a connection line 38, valve 34B is fluidically coupled to valve 34A via connection line 36, and valve 34A is fluidically coupled to the pump 50 via connection line 40. Alternatively, the valve system 34 and the pump 50 can be fluidically coupled to each other by any configuration of connection lines. The specific operation of the valve system 34 and in the context of the system 10 will be explained in further detail below.

Each valve 34A, 34B, 34C of the valve system 34, in one specific embodiment, is a known, commercially available valve such as a solenoid valve. Alternatively, each valve 34A, 34B, 34C can be any known valve for use in fluidic systems that can operate to move between an open and a closed position in a known fashion to control flow of a fluid such as air.

In addition to being fluidically coupled to the valve system 34, the intake lines 32A, 32B, 32C, and the intake structure 12, the pump 50 is also fluidically coupled to a detection assembly 54 via a connection line 52. In one embodiment, the detection assembly 54 includes both a UV illumination lamp 56 and a photon-sensitive sensor 58. The lamp 56 and sensor 58 can both be known components used in similar VOC-detection systems, such as, for example, the various handheld VOC sensing devices sold by GrayWolf Sensing Solutions, LLC, which is located in Shelton, Conn. Alternatively, the lamp 56 and sensor 58 can be separate components that are not part of an assembly. In operation, the assembly 54 receives the sample air via the connection line 52 from the pump 50. Alternatively, the positions of the pump 50 and the assembly 54 can be switched within the system 10 such that the pump 50 is positioned "downstream" from the assembly 54. In this configuration, the assembly 54 receives the sample air via the connection line 40 from valve 34A and subsequently the pump 50 receives the air via the connection line 52 from the assembly 54.

The lamp 56 and sensor 58 operate in a fashion similar to known detection systems, with the lamp 56 exciting the electrons of any VOC molecules present in the sample that has been pumped into the assembly 54 and the sensor 58 detecting the resulting discharged photons as described above. According to one embodiment, the pump 50 is configured to maintain a constant laminar air flow across the detection assembly 54 to achieve constant and consistent detection results.

The detection assembly 54 is fluidically coupled to the exhaust structure 72 via the connection line 70, according to certain implementations. The exhaust structure 72, according to one embodiment, contains a filter 74 through which the air passes before exiting from the exhaust port 76. In one embodiment, the filter 74 is a carbon filter 74 that ensures that the air exhausted from the system 10 contains no VOCs, thereby preventing delivery of contaminants back into the test area. Alternatively, the filter 74 can be a hybrid filter, such as certain filters sold by Green Ladder Technologies, LLC, located in Batavia, Ill. In a further alternative, the exhaust structure 72 can utilize other purification components or methods, such as application of bottled gas (such as oxygen), electrolysis, or any other known purification method or device. According to a further alternative, the exhaust structure 72 can also serve as an exhaust muffler by muffling the sound of the air being exhausted from the system 10 using any known muffler component or muffling technology.

In addition, the detection assembly 54 is also electrically and electronically coupled to the controller 60 via a communication line 62. In certain embodiments, the communication line 62 can also be a power line 62 or can be coupled with a power line (not shown). The communication line 62 allows for the detection assembly 54 to transmit collected data to the controller 60 and for the controller 60 to transmit information (including, for example, operational instructions) to the detection assembly 54.

The controller 60, according to one embodiment, is a processor 60. Alternatively, the controller 60 can have a processor and memory integrated into the controller 60, along with other known components or features.

The system 10 also has a valve controller 64. The valve controller 64 is electronically coupled to the controller 60 via the communication line 66 and also to the valve system 34 via communication line 68. According to certain embodiments, the valve controller 64 transmits the "firing" or valve actuation instructions to the valve system 34, thereby controlling the configuration of each of the valves 34A, 34B, 34C as the intake system 30 operates to control intake of air from the intake structure 12 or the three intake lines 32A, 32B, 32C as will be discussed in further detail below. Alternatively, the valve controller 64 is part of the controller 60. In a further alternative, there is no separate valve controller and the controller 60 controls the valve system 34.

In accordance with certain alternative implementations, the system 10 can also have one or more additional sensors (not shown) coupled to or otherwise associated with the housing 8 that is/are configured to detect other parameters in the target space. For example, the sensor can be a temperature sensor, an air particulate sensor, or a humidity sensor. Alternatively, the sensor can be any known sensor that can be used to detect or otherwise monitor any characteristic of interest in the target space. In accordance with certain embodiments, the various systems herein can incorporate an air particulate sensor or detection system instead of (or in addition to) the VOC detection systems disclosed herein and can operate in a similar fashion, with cycles of (1) testing air samples for air particulates and (2) calibration/recalibration.

In one implementation, the system 10 is powered by the power cord 90 mentioned above, which is a standard 110-volt AC power cord 90. Alternatively, any known electrical power cord or other power source can be used, including, for example, batteries.

The system 10, according to one embodiment, has the communication line 92 discussed above connecting the controller 60 to an external system 94, such as an external computer 94. In one implementation, the communication line 92 is a "Cat 5" cord or any other known communication line or coupling component for coupling the processor 60 to any external system 94. Alternatively, the system 10 can be coupled wirelessly to such an external system 94.

According to one alternative embodiment as best shown in FIG. 2, the system 10 can have a carbon casing 96 disposed around the housing 8 to add an additional level of protection against impurities. In other words, the system 10 can have a carbon casing (such as a box or any other type of structure) 96 fully enclosing the base unit 8 such that the base unit 8 is disposed within the structure 96. It is understood that the carbon casing 96 can be comprised mainly of carbon, or alternatively can be made of any known purifying material to provide the same level of protection as described herein. The carbon casing 96 protects against any leaks or structural issues that could cause subsequent leaks within the system 10 that could allow for impurities to enter into any portion of the system and thereby render the resulting data from the system 10 inaccurate. This protection would result from the carbon casing 96 purifying any air passing through the casing 96 that might then enter into the housing 8 or some component thereof via some leak therein. In a further alternative, the base unit 8 could be the carbon casing 8. That is, the walls of the housing 8 could be made of carbon or a similar known purifying material to provide this protection against leaks.

In use, according to certain implementations, the system 10 provides repeating cycles of calibration/recalibration and air testing of a target area. More specifically, the system 10 performs repeating cycles in which the detection system 54 is first calibrated using purified air and then the air of two or more locations within the target area is collected via the intake system 30 and tested via the recently-calibrated detection system 54. This repeated calibration/recalibration step makes it possible to provide accurate and precise measurements of VOC concentrations at not only low levels (ppm), but also ultra-low levels (ppb). It is understood that the terms "calibration" and "recalibration" can be used interchangeably herein to mean any step of calibrating the detection system 54 as described herein. It is generally understood that the first calibration of the system 54 is known as a calibration step and that the second and every subsequent calibration can be known as a calibration step or a recalibration step.

The first step in the cycle, in certain implementations, relates to the system 10 being calibrated/recalibrated (or "zeroed") to compensate for the skewed measurements caused by VOCs sticking to the UV-illumination device as described above as a result of ongoing use of the system 10. The recalibration process can occur as follows. First, a control or reference sample of air is allowed to enter the intake structure 12 and pass through the zero filter 16 therein, thereby eliminating any VOCs present in the control sample and resulting in pure (0 ppb) reference air. In this step, the first valve 34A is set such that the intake structure 12 is in fluid communication with the pump 50, thereby resulting in the purified reference air passing through the connection line 18, through the first valve 34A, through the pump 50 via connection line 48 and into the detection assembly 54 via the connection line 52.

At this point, the detection process occurs with respect to the reference sample of air. That is, the detection assembly 54 is actuated such that the UV-illumination lamp 56 generates a reference number of photons that are detected by the sensor 58. The resulting measurement corresponds to a zero reference sensor voltage reading that is consistent with a "0" ppb measurement—it is the reference amount of voltage that indicates a reading of 0 ppb of VOCs. This zero reference reading is transmitted to the controller 60 and stored therein such that the reading then becomes the base reading to which all subsequent readings of test samples from the input lines 32A, 32B, 32C are compared by the controller 60 to accurately determine the VOC concentration in those test samples. That is, with the zero reference voltage reading set, the controller 60 compares the subsequent readings of VOC concentrations from test samples to the zero reference amount such that the difference between the test sample reading and the zero reference reading is an increased sensor voltage amount that indicates the concentration of VOCs in the test sample.

In contrast, known technologies have no such real-time calibration step. That is, the known systems and devices do not—during ongoing operation—monitor or otherwise account for the adherence of the VOC molecules to the sensor and the subsequent deleterious effect on the sensor and thus the accuracy of the device/system.

Once the recalibration process has been completed, the sample testing process begins. That is, after the recalibration, the first valve 34A is moved (by the controller 60, according to one embodiment) to a second configuration (or "closed") (in comparison to its configuration during the recalibration step) such that air from the intake structure 12 cannot enter the pump 50 or the detection assembly 54. In this second configuration, the valve 34A instead allows for fluidic access solely between the intake line 32A and the pump 50 such that sample air from intake line 32A is urged through the pump 50 and into the detection assembly 54. At this point, the assembly 54 is actuated and the sample voltage reading is recorded and transmitted to the controller 60, which compares the test sample reading to the zero reference amount and thereby calculates a VOC concentration in ppb and stores the calculation in memory associated with the controller 60. In addition, in certain embodiments, the controller 60 transmits the information to the electronic display 78 mentioned above on an external portion of the system 10 as best shown in FIG. 1 such that the concentration can be read by a user. When the measurement process is complete, the pump 50 urges the test sample air out through the exhaust structure 72 such that the air passes through the exhaust filter 74 and is expelled out of the port 76.

After testing the first intake 32A sample, a testing sample from the second intake line 32B is tested. That is, the controller 60 actuates the first valve 34A to move back to the first (or "closed") configuration and further actuates the second valve 34B to move to an "open" configuration which allows for fluidic access between the second intake line 32B and the pump 50 such that the sample air from the second intake line 32B is urged through the pump 50 and into the detection assembly 54. The assembly 54 is again actuated, and the process is similar to that described above with respect to the testing sample from the first intake line 32A. That is, the sample voltage reading is recorded and transmitted to the controller 60, which compares the test sample reading to the zero reference amount and thereby calculates a VOC concentration in ppb and stores the calculation in memory associated with the controller 60. In addition, the controller 60 may also transmit the information to the electronic display 78 such that the concentration from the second intake line 32B can be read by a user. When the measurement process is complete, the pump 50 urges the test sample air out through the exhaust structure 72 such that the air passes through the exhaust filter 74 and is expelled out of the port 76.

It is understood that this process of sample testing occurs with respect to air samples from every intake line of the system 10. In this specific embodiment as depicted in FIGS. 1 and 2, the sample from the third intake line 32C would tested in a manner similar to that described above with respect to the samples from the first and second intake lines 32A, 32B. In other embodiments having more than three intake lines, the same process would be repeated for each of those additional samples from each of those additional intake lines.

According to one embodiment, once all the samples from all of the intake lines have been tested, the cycle is complete and a new cycle begins with the system 10 being recalibrated again according to the same or similar recalibration steps as those described above. Again, known systems/devices have no such repeated calibration during operation. Once that recalibration process is completed and a new zero reference reading has been determined, the new zero reference reading is used for the next round of sample testing as part of the second cycle. And this repetition of the cycle of recalibration and testing continues indefinitely. In some embodiments, the repeated cycles continue until the UV illumination lamp 56 is rendered inoperable or the detection results are rendered unusable as a result of the number of VOC molecules adhered to the lamp.

Each cycle, in some embodiments, can take about 10 minutes, such that the system 10 performs six cycles per hour. Alternatively, the speed of each cycle can vary from about 0.5 seconds to about an hour or more. In a further alternative, each cycle can vary from about 1 second to about 15 minutes. In yet another alternative, each cycle can take at least 10 seconds. It is understood that the cycle time can be adjusted as desired. In one embodiment, the cycle time can be any time that ensures that the recalibration occurs often enough to maintain the accuracy and precision of the VOC concentration detection.

The repeating cycles of calibration/re-calibration and testing, according to one embodiment, provide for extended use of the system embodiments disclosed or contemplated herein long beyond the effective life of any known systems/devices. Thus, the various system and device embodiments herein provide for continuous or semi-continuous monitoring of VOCs. That is, "continuous monitoring," as used herein, means the monitoring of VOCs at a location with a single device/system via the cycles of calibration and testing over an extended period of time despite the ongoing buildup of VOC molecules on the sensor of the device/system without any interruption in the sampling (other than the calibration step incorporated into each cycle). In certain implementations, the various system/device embodiments disclosed or contemplated herein can provide continuous monitoring of VOCs for up to one year or even longer without losing accuracy as a result of the recalibration process described herein. This accuracy makes it possible for the various embodiments herein to continuously monitor VOC levels accurately and precisely down to not only low VOC levels (ppm), but also to ultra-low levels (ppb) for the entire life of the device.

Further, "semi-continuous monitoring," as used herein, means the monitoring of VOCs at intermittent periods with interruption due to calibration, the monitoring of alternative locations, or predetermined delays or reductions in the frequency of the monitoring cycles. When a system/device herein operates under semi-continuous monitoring, the time duration for monitoring VOCs in each location and/or for calibration can be adjusted based on the environment and other factors.

Depending on the circumstances and factors involved in the use of the system/device, if the change in VOC concentration occurs very quickly as within a chemical reaction, the system/device may use continuous monitoring. In contrast, in certain applications of the system/device in which the VOC concentration changes over longer periods of time (i.e., hour or days), the system/device may use semi-continuous monitoring. In certain embodiments in a fashion similar to signal to noise ratio ("SNR") practice, the monitoring frequency should be at least twice the VOC rate of change to accurately reproduce the change in VOC concentration.

In accordance with certain implementations, upon the completion of each cycle of calibration and measurements from each intake line, the data is sent from the controller 60 to an external system 94 via the communication line 92. Alternatively, the data can be transmitted to the external system 94 at any time during the process. The external system 94 can further process the date, issue alerts to predetermined users or recipients based on certain preset limits being exceeded (or other similar parameters), and/or analyze the data. Further, the external system 94 can have a website or any other known interface (including, for example, an application on a mobile device) that can be used to access the external system 94 and the system 10 described above via other distributed computers. In certain embodiments, the external system 94 can transmit the alerts to one or more predetermined recipients, such as users, customers, or technicians. Such information or instructions can be inputted into the external system 94 via the interface, such as a website or mobile device. For example, a user (such as, for example, a customer) can access the external system 94 via the interface to insert specific parameters to trigger an alert to the user (or someone else). The external system 94 can transmit the alert via e-mail, text message, application alert, phone call, or any other known medium. Further, a user can use the interface—such as a mobile device application or website, for example—to track real-time data or data over some period of time. That is, the interface can not only provide real-time VOC concentration data or other real-time information, but can also provide VOC concentration date or other information over time.

Figure 3A:
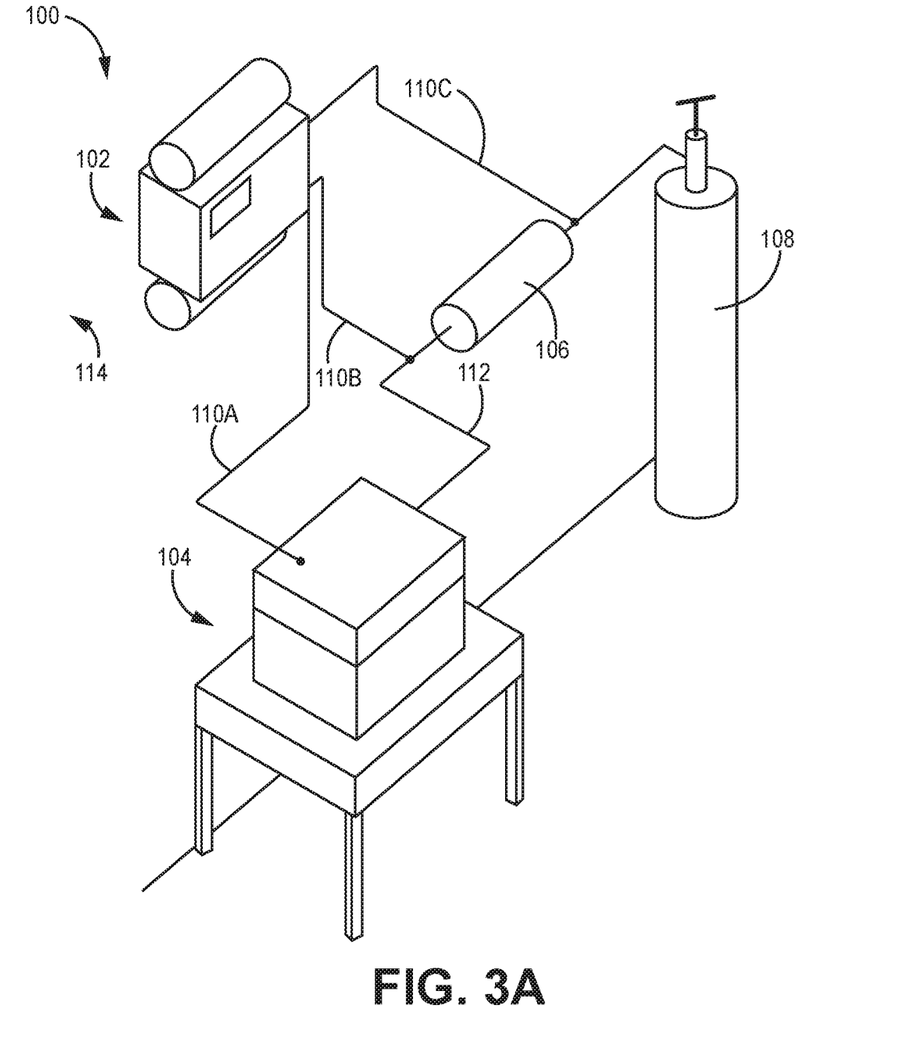
FIG. 3A is a perspective view of a lab setting containing a VOC monitoring system, according to one embodiment.

In accordance with a further embodiment, as best shown in FIG. 3A, a VOC monitoring system 102 similar to the system 10 described above can be used in various specific equipment-monitoring applications, including, for example, industrial, medical, or research lab applications. That is, the various system and device embodiments herein can be used to measure VOC levels in highly sensitive equipment in a number of settings, including medical, industrial, and research equipment. In this specific example, the system 102 is used to test and track the useful life of a filter 106 in an incubator system 104 in a lab setting 100. According to one embodiment, the lab setting 100 is an in-vitro fertilization lab 100. Alternatively, the system 102 could be used to test any equipment that requires such testing in any setting. Specific additional examples of the type of equipment that could be tested/monitored by a VOC monitoring system according to the embodiments disclosed or contemplated herein include, but are certainly not limited to, laboratory fume hoods and kitchen exhaust equipment.

In this particular embodiment, the system 102 is positioned on a wall 114 of the lab 100. Alternatively, the system 102 can be positioned in any desired location and potentially a substantial distance away from the incubator system 104 (or other device/system to be tested) depending on the length of the intake lines 110A, 110B, 110C and the desired positioning of the system 102.

In this exemplary implementation, the system 102 is used to test and track the useful life of the filter 106 in the known incubator system 104. More specifically, the exemplary incubator system 104 operates in part by injecting a regulated gas (contained in the gas cylinder 108) into the incubator 104 via a gas line 112 after urging the gas through the inline filter 106 fluidically coupled to the gas line 112 to purify the gas or reduce the amount of contaminants therein. To accomplish this, the three intake lines 110A, 110B, 110C are attached to different portions of the incubator system 104 in order to test air samples from each of those portions. That is, the first intake line 110A is fluidically coupled to the incubator 104 such that gas can be collected from the incubator 104 and thereby test the VOC level within the incubator 104. Further, the second intake line 110B is fluidically coupled to gas line 112 downstream from the filter 106 such that gas can be collected that has already passed through the inline filter 106 in the system 104. Finally, the third intake line 110C is fluidically coupled to the gas line 112 upstream from the filter 106 such that gas can be collected that has not yet passed through the filter 106. Thus, the system 102 measures the VOC level in the gas both before and after the gas has been filtered via the inline filter 106. Further, it is understood that this system 102 can operate in a similar fashion to the system 10 embodiment discussed above, with repeating cycles of testing and calibration.

In use, the system 102 can be used to monitor the useful life of the filter 106 in the incubator system 104. During operation of the incubator system 104, it is understood that a new filter 106 will be capable of removing most, if not all, impurities from the gas such that the VOC level in the gas exiting the filter 106 is very small to zero. However, it is further understood that as the incubator system is used over a period of time, that same filter 106 will begin to become increasingly less effective such that the VOC concentration in the gas exiting the filter 106 will increase until, at some point, the gas wil have the same VOC level as the gas that enters the filter 106 (meaning that the filter 106 is completely spent and thus is no longer effective to remove any VOCs from the gas). As such, it is understood that this difference in VOC level between the gas entering the filter 106 and the gas exiting the filter 106 quantifies the life remaining within the filter 106. In this context, the system 102 can be used to track the filter 106 life by being coupled to and collecting the VOC concentration information at various points within the incubation system 104 as described above. By collecting the gas samples both before and after the gas passes through the filter 106 over time, the system 102 can track the effectiveness of the filter 106 over time and identify the point at which the old filter 106 needs to be replaced with a new filter.

Figure 3B:
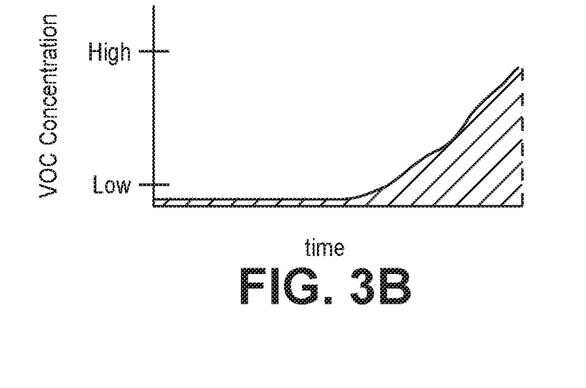
FIG. 3B is a line chart depicting the life cycle of a filter in an incubator system, according to one embodiment.

One example of this filter life tracking is shown graphically in FIG. 3B. The graph depicts concentration of VOCs detected in the filtered gas over time, thereby depicting the effectiveness of the filter 106. As shown in the graph, it is generally understood that the time to replace the filter 106 can be identified as the period where the VOC concentration in the gas is still low but is starting to increase.

According to one embodiment, the filter life tracking data can be collected, recorded by the controller (not shown, but similar to the controller 60 discussed above in system 10), transmitted to an external system 94, and used to trigger an alert (via e-mail, text, or any other known medium) that can be transmitted to an appropriate user (such as, for example, a customer that owns the incubation system 104) to notify the user that the filter 106 should be changed. In a further implementation, the customer can access the external system 94 via a website interface to set its own VOC limits that will trigger the alert. In addition, the customer could also use the website interface to view real-time VOC concentration measurements as well as VOC concentration measurements over time.

Although the present invention has been described with reference to preferred embodiments, persons skilled in the art will recognize that changes may be made in form and detail without departing from the spirit and scope of the invention.

What is claimed is:

1. A volatile organic compound ("VOC") monitoring system comprising:
   (a) a housing;
   (b) a reference air intake component associated with the housing, the air intake component comprising an intake air purification device;
   (c) an air sample intake system associated with the housing, the air sample intake system comprising at least one sample intake line;
   (d) at least one valve coupled to the at least one sample intake line and the reference air intake component;
   (e) an air pump fluidically coupled to the reference air intake component and the at least one sample intake line via the at least one valve;
   (f) a detection assembly fluidically coupled to the air pump; and
   (g) an exhaust component associated with the housing, the exhaust component comprising an exhaust air purification device fluidically coupled to the detection assembly.

2. The VOC monitoring system of claim 1, wherein the at least one sample intake line comprises a first sample intake line and a second sample intake line.

3. The VOC monitoring system of claim 2, wherein first and second sample intake lines are operably coupled to a piece of equipment.

4. The VOC monitoring system of claim 3, wherein the piece of equipment is an incubator.

5. The VOC monitoring system of claim 2, wherein the first sample intake line comprises a first intake opening disposed at a first location in a space and the second sample intake line comprises a second intake opening disposed at a second location in the space, wherein the first and second locations are separated by at least 5 feet.

6. The VOC monitoring system of claim 5, wherein the first and second locations are separated by at least 50 feet.

7. The VOC monitoring system of claim 2, wherein the at least one valve comprises
   (a) a first valve coupled to the first sample intake line, the reference air intake component, and the air pump; and
   (b) a second valve coupled to the second sample intake line and the first valve.

8. The VOC monitoring system of claim 1, wherein the at least one valve comprises
   (a) a first position in which the reference air intake component is in fluidic communication with the air pump; and
   (b) a second position in which the first sample intake line is in fluidic communication with the air pump.

9. The VOC monitoring system of claim 1, wherein the at least one sample intake line comprises a plurality of sample intake lines comprising a plurality of intake openings disposed at a plurality of locations.

10. A VOC detection system comprising:
(a) a reference air intake system comprising an intake air purification device;
(b) a valve system comprising at least first and second valves, wherein the first valve is coupled to the intake air purification device;
(c) an air sample intake system comprising at least first and second sample intake lines, wherein the first sample intake line is coupled to the first valve and the second sample intake line is coupled to the second valve;
(d) a detection assembly coupled to the intake air purification device and the sample intake system, the detection assembly comprising:
  (i) an illumination lamp; and
  (ii) a photon-sensitive sensor;
(e) an air pump coupled to the intake air purification device, the sample intake system, and the detection assembly;
(f) an exhaust component comprising an exhaust air purification device coupled to the detection assembly; and
(g) a controller electronically coupled to the detection assembly.

11. The VOC detection system of claim 10, wherein the first valve comprises:
(a) a first position in which the intake air purification device is in fluidic communication with the air pump and the detection assembly; and
(b) a second position in which the first sample intake line is in fluidic communication with the air pump and the detection assembly.

12. The VOC detection system of claim 11, wherein the second valve comprises:
(a) a first position in which the second sample intake line is not in fluidic communication with the air pump and the detection assembly; and
(b) a second position in which the second sample intake line is in fluidic communication with the air pump and the detection assembly.

13. The VOC detection system of claim 12, further comprising a third valve and a third sample intake line coupled to the third valve, wherein the third valve comprises:
(a) a first position in which the third sample intake line is not in fluidic communication with the air pump and the detection assembly; and
(b) a second position in which the third sample intake line is in fluidic communication with the air pump and the detection assembly.

14. The VOC detection system of claim 10, wherein the a detection assembly is configured to detect low parts per million VOC concentrations and ultra low parts per billion VOC concentrations.

15. A method of monitoring VOCs, the method comprising:
positioning a VOC monitoring system such that the VOC monitoring system can receive samples from a target volume, wherein the VOC monitoring system comprises:
  (a) an intake air purification device;
  (b) at least one sample intake line;
  (c) a detection assembly coupled to the intake air purification device and the at least one sample intake line; and
  (d) a controller coupled to the detection assembly;
calibrating the system by causing a calibration sample to pass through the intake purification device and the detection assembly, measuring a first zero reference reading with the detection assembly, and transmitting the first zero reference reading to the controller;
testing an air sample by causing the air sample to pass through the at least one sample intake line and the detection assembly, measuring a sample reading with the detection assembly, transmitting the sample reading to the controller, and calculating a VOC concentration with the controller based on the sample reading and the first zero reference reading;
recalibrating the system by causing a recalibration sample to pass through the intake purification device and the detection assembly, measuring a second zero reference reading with the detection assembly, and transmitting the second zero reference reading to the controller; and
repeating the testing and recalibrating steps.

16. The method of claim 15, wherein the causing the calibration sample to pass through the intake purification device and the detection assembly further comprises:
actuating a valve to move into a first position in which the intake purification device is in fluidic communication with the detection assembly; and
actuating a pump to urge the calibration sample through the intake purification device and the detection assembly.

17. The method of claim 16, wherein the causing the air sample to pass through the at least one sample intake line and the detection assembly further comprises:
actuating the valve to move into a second position in which the at least one sample intake line is in fluidic communication with the detection assembly; and
actuating the pump to urge the air sample through the at least one sample intake line and the detection assembly.

18. The method of claim 15, further comprising transmitting an alert to a user when the VOC concentration exceeds a predetermined level.

19. The method of claim 18, further comprising establishing the predetermined level at an interface, wherein the interface is operably coupled with the controller.

20. The method of claim 15, wherein the target volume is a volume in a piece of equipment, wherein the testing the air sample comprises testing a first air sample from an entrance of a filter and testing a second air sample from an exit of the filter, wherein the method further comprises tracking a life of the filter.

* * * * *